(12) United States Patent
Chong

(10) Patent No.: US 10,408,600 B2
(45) Date of Patent: Sep. 10, 2019

(54) OPTICAL COHERENCE TOMOGRAPHY WITH A FIZEAU-TYPE INTERFEROMETER

(71) Applicant: SANTEC CORPORATION, Komaki, Aichi (JP)

(72) Inventor: Changho Chong, Los Altos, CA (US)

(73) Assignee: SANTEC CORPORATION, Komaki (JP)

( * ) Notice: Subject to any disclaimer, the term of this patent is extended or adjusted under 35 U.S.C. 154(b) by 18 days.

(21) Appl. No.: 15/630,654

(22) Filed: Jun. 22, 2017

(65) Prior Publication Data

US 2018/0372478 A1   Dec. 27, 2018

(51) Int. Cl.
*G01B 9/02* (2006.01)
*G01B 11/24* (2006.01)
*G01N 21/47* (2006.01)

(52) U.S. Cl.
CPC ..... *G01B 9/02091* (2013.01); *G01B 9/02002* (2013.01); *G01B 9/02025* (2013.01); *G01B 9/02057* (2013.01); *G01B 11/2441* (2013.01); *G01N 21/4795* (2013.01)

(58) Field of Classification Search
CPC ................. G01B 2290/25; G01B 9/02091
See application file for complete search history.

(56) References Cited

U.S. PATENT DOCUMENTS

| 4,466,699 A | 8/1984 | Droessler et al. |
| 5,022,745 A | 6/1991 | Zayhowski et al. |
| 5,319,668 A | 6/1994 | Luecke |
| 5,372,135 A | 12/1994 | Mendelson et al. |
| 5,430,574 A | 7/1995 | Tehrani |
| 5,537,162 A | 7/1996 | Hellmuth et al. |
| 5,561,523 A | 10/1996 | Blomberg et al. |

(Continued)

FOREIGN PATENT DOCUMENTS

| DE | 10 2011 114 797 A1 | 4/2013 |
| JP | 2006-202543 A | 8/2006 |

(Continued)

OTHER PUBLICATIONS

Changho Chong, et al. "Large Coherence Length Swept Source for Axial Length Measurement of the Eye." Applied Optics 48:10 (2009): D145-150.

(Continued)

*Primary Examiner* — Jonathan M Hansen
(74) *Attorney, Agent, or Firm* — Foley & Lardner LLP

(57) ABSTRACT

An OCT system includes a light source configured to generate an optical beam, a Fizeau-type interferometer configured to receive the optical beam and produce an interference pattern, a detector configured to receive the interference pattern and produce an image signal, and a processing circuit including a processor and a memory, the memory being structured to store instructions that are executable by the processor to cause the processor to receive the image signal from the detector and generate an OCT image based on the image signal. The Fizeau-type interferometer includes a scanning element configured to receive the optical beam and direct the optical beam in a plurality of directions towards a sample and a reflective element configured to divide the directed optical beam into a reference beam and a sample beam that reflects off of a surface of a sample.

17 Claims, 5 Drawing Sheets

(56) References Cited

U.S. PATENT DOCUMENTS

| | | | |
|---|---|---|---|
| 5,979,760 A | 11/1999 | Freyman et al. | |
| 5,982,963 A | 11/1999 | Feng et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,275,718 B1 | 8/2001 | Lempert | |
| 6,282,011 B1 | 8/2001 | Tearney et al. | |
| 6,373,632 B1 | 4/2002 | Flanders | |
| 6,421,164 B2 | 7/2002 | Tearney et al. | |
| 6,485,413 B1 | 11/2002 | Boppart et al. | |
| 6,501,551 B1 | 12/2002 | Tearney et al. | |
| 6,564,087 B1 | 5/2003 | Pitris et al. | |
| 7,099,358 B1 | 8/2006 | Chong | |
| 7,231,243 B2 | 6/2007 | Tearney et al. | |
| 7,323,680 B2 | 1/2008 | Chong | |
| 7,324,214 B2 * | 1/2008 | De Groot | G01B 11/0675 356/497 |
| 7,352,783 B2 | 4/2008 | Chong | |
| 7,382,809 B2 | 6/2008 | Chong et al. | |
| 7,388,891 B2 | 6/2008 | Uehara et al. | |
| 7,400,410 B2 | 7/2008 | Baker et al. | |
| 7,414,779 B2 | 8/2008 | Huber et al. | |
| 7,428,057 B2 * | 9/2008 | De Lega | G01B 9/023 356/497 |
| 7,489,713 B2 | 2/2009 | Chong et al. | |
| 7,701,588 B2 | 4/2010 | Chong | |
| 7,725,169 B2 | 5/2010 | Boppart et al. | |
| 7,835,010 B2 | 11/2010 | Morosawa et al. | |
| 7,865,231 B2 | 1/2011 | Tearney et al. | |
| 7,869,057 B2 * | 1/2011 | De Groot | G01B 9/02044 356/511 |
| 7,884,945 B2 | 2/2011 | Srinivasan et al. | |
| 7,961,312 B2 | 6/2011 | Lipson et al. | |
| 8,036,727 B2 | 10/2011 | Schurman et al. | |
| 8,115,934 B2 | 2/2012 | Boppart et al. | |
| 8,315,282 B2 | 11/2012 | Huber et al. | |
| 8,405,834 B2 | 3/2013 | Srinivasan et al. | |
| 8,427,649 B2 | 4/2013 | Hays | |
| 8,500,279 B2 | 8/2013 | Everett et al. | |
| 8,625,104 B2 | 1/2014 | Izatt et al. | |
| 8,690,328 B1 | 4/2014 | Chong | |
| 8,690,330 B2 | 4/2014 | Hacker et al. | |
| 9,163,930 B2 | 10/2015 | Buckland et al. | |
| 9,851,433 B2 | 12/2017 | Sebastian | |
| 2002/0163948 A1 | 11/2002 | Yoshida et al. | |
| 2005/0171438 A1 | 8/2005 | Chen et al. | |
| 2005/0201432 A1 | 9/2005 | Uehara et al. | |
| 2005/0213103 A1 | 9/2005 | Everett et al. | |
| 2006/0105209 A1 | 5/2006 | Thyroff et al. | |
| 2006/0109872 A1 | 5/2006 | Sanders | |
| 2006/0215713 A1 | 9/2006 | Flanders et al. | |
| 2007/0040033 A1 | 2/2007 | Rosenberg | |
| 2007/0076217 A1 | 4/2007 | Baker et al. | |
| 2007/0081166 A1 | 4/2007 | Brown et al. | |
| 2007/0133647 A1 | 6/2007 | Daiber | |
| 2007/0141418 A1 | 6/2007 | Ota et al. | |
| 2007/0291277 A1 | 12/2007 | Everett et al. | |
| 2008/0269575 A1 | 10/2008 | Iddan | |
| 2009/0022181 A1 | 1/2009 | Atkins et al. | |
| 2009/0103050 A1 | 4/2009 | Michaels et al. | |
| 2009/0169928 A1 | 7/2009 | Nishimura et al. | |
| 2009/0268020 A1 | 10/2009 | Buckland et al. | |
| 2009/0290613 A1 | 11/2009 | Zheng et al. | |
| 2010/0157308 A1 | 6/2010 | Xie | |
| 2010/0246612 A1 | 9/2010 | Shimizu | |
| 2010/0284021 A1 | 11/2010 | Hacker | |
| 2011/0228218 A1 | 9/2011 | Hauger et al. | |
| 2011/0235045 A1 * | 9/2011 | Koerner | G02B 21/0056 356/451 |
| 2011/0255054 A1 | 10/2011 | Hacker et al. | |
| 2011/0299034 A1 | 12/2011 | Walsh et al. | |
| 2012/0026466 A1 | 2/2012 | Zhou et al. | |
| 2012/0136259 A1 | 5/2012 | Milner et al. | |
| 2012/0188555 A1 | 7/2012 | Izatt et al. | |
| 2013/0265545 A1 | 10/2013 | Buckland et al. | |
| 2014/0051952 A1 | 2/2014 | Reichgott et al. | |
| 2014/0111774 A1 | 4/2014 | Komine | |
| 2014/0228681 A1 | 8/2014 | Jia et al. | |
| 2014/0293290 A1 | 10/2014 | Kulkarni | |
| 2015/0348287 A1 | 12/2015 | Yi et al. | |
| 2016/0178346 A1 | 6/2016 | Kulkarni | |
| 2018/0088236 A1 | 3/2018 | Eichenholz et al. | |
| 2018/0128594 A1 * | 5/2018 | Lee | G01B 9/02091 |

FOREIGN PATENT DOCUMENTS

| | | |
|---|---|---|
| JP | 2008-188047 | 8/2008 |
| JP | 2010-172538 | 8/2010 |
| WO | WO-2012/075126 A2 | 6/2012 |
| WO | WO-2013/168149 A1 | 11/2013 |
| WO | WO-2015/121756 A2 | 8/2015 |
| WO | WO-2017/176901 A1 | 10/2017 |

OTHER PUBLICATIONS

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

Dai et al., "Optical coherence tomography for whole eye segment imaging," Optics Express, vol. 20, No. 6 (2012) pp. 6109-6115.

Dhalla et al., "Simultaneous swept source optical coherence tomography of the anterior segment and retina using coherence revival," Optics Letters, vol. 37 No. 11, Jun. 1, 2012, pp. 1883-1885.

Dhalla, et al., "Simultaneous swept source optical coherence tomography of the anterior segment and retina using coherence revival," Optics Letters, 2012, vol. 37, No. 11, pp. 1883-1885.

English Translation of the International Search Report and Written Opinion on International Application No. PCT/EP2009/009189, dated Apr. 6, 2010, 12 pages.

F. Lexer et al., "Wavelength-tuning interferometry of intraocular distances," Applied Optics, vol. 36, No. 25, pp. 6548-6553 (Sep. 1, 1997).

Fainman, Y. et al., "Nanophotonics for Information Systems," Information Optics and Photonics (T. Fournel and B. Javidi eds., Springer New York, 2010) pp. 13-37.

International Preliminary Report on Patentability in corresponding international application No. PCT/US2015/019299 dated Sep. 22, 2016.

International Preliminary Report on Patentability in corresponding international application No. PCT/US2015/032727 dated Dec. 8, 2016.

International Preliminary Report on Patentability in International appln. No. PCT/IB2015/000808.

International Search Report and Written Opinion dated Aug. 26, 2015 for PCT/US15/32727 (8 pages).

International Search Report and Written Opinion in corresponding application No. PCT/US2016/035012 dated Aug. 18, 2016.

International Search Report and Written Opinion in International Application No. PCT/US2015/19299 dated Nov. 2, 2015 (10 pages).

International Search Report and Written Opinion in PCT/IB2015/000808 dated Oct. 20, 2015 (12 pages).

Jeong et al., "Spectral-domain OCT with dual illumination and interlaced detection for simultaneous anterior segment and retina imaging," Optics Express, vol. 20, Issue 17, pp. 19148-19159 (2012).

Jia et al., Split-Spectrum Amplitude-Decorrelation Angiography with Optical Coherence Tomography, Optics Express, vol. 20 No. 4, Feb. 9, 2012, pp. 4710-4725.

Lexer et al., "Wavelength-tuning interferometry of intraocular distances", Applied Optics, vol. 36, No. 25, Sep. 1, 1997, pp. 6548-6553.

Mariampillai et al., Speckle Variance Detection of Microvasculature Using Swept-Source Optical Coherence Tomography, Optics Letters, vol. 33 No. 13, Jul. 1, 2008, pp. 1530-1532.

Nankivil et al.,"Handheld, rapidly switchable, anterior/posterior segment swept source optical coherence tomography probe," OSA

(56) References Cited

OTHER PUBLICATIONS

Nov. 1, 2015; vol. 6, No. 11; DOI:10.1364/BOE.6.004516; Biomedical Optics Express 4516-4528.
Non-Final Rejection on U.S. Appl. No. 14/723,325 dated Dec. 7, 2017.
P. Tayebati et al., "Microelectromechanical tunable filter with stable half symmetric cavity," Electronics Letters, vol. 34, No. 20, pp. 1967-1968 (Oct. 1, 1998).
Poddar, et al., "Non-Invasive Glucose Monitoring Techniques: A Review and Current Trends," Oct. 31, 2008, pp. 1-47.
Sarlet, G. et al., "Wavelength and Mode Stabilization of Widely Tunable SG-DBR and SSG-DBR Lasers," IEEE Photonics Technology Letters, vol. 11, No. 11, Nov. 1999, pp. 1351-1353.
Segawa, Toru et al., "Semiconductor Double-Ring-Resonator-Coupled Tunable Laser for Wavelength Routing," IEEE Journal of Quantum Electronics, vol. 45, No. 7, Jul. 2009, pp. 892-899.
Sergie Ortiz, et al. "Corneal Topography From Spectral Optical Coherence Tomography (SOCT)." Biomedical Optics Express 2:12, (2011):3232-3247.
U.S. Notice of Allowance dated Dec. 6, 2013.
U.S. Notice of Allowance on U.S. Appl. No. 14/601,945 dated Sep. 13, 2016.
U.S. Office Action dated Sep. 12, 2013.
U.S. Office Action dated Aug. 19, 2015.
U.S. Office Action on U.S. Appl. No. 14/601,945 dated Mar. 2, 2016.
U.S. Office Action on U.S. Appl. No. 14/613,644 dated Jun. 8, 2016.
U.S. Office Action on U.S. Appl. No. 14/641,200 dated Mar. 14, 2016.
U.S. Office Action on U.S. Appl. No. 14/641,200 dated Dec. 7, 2015.
U.S. Office Action on U.S. Appl. No. 14/723,325 dated Nov. 18, 2016.
U.S. Office Action on U.S. Appl. No. 15/202,925 dated Jul. 27, 2017.
Non-Final Office Action on U.S. Appl. No. 15/648,239 dated Jun. 6, 2018.
U.S. Notice of Allowance on U.S. Appl. No. 15/202,925 dated May 17, 2018.
International Search Report and Written Opinion in International Application No. PCT/US2019/027671, dated Jul. 1, 2019. (9 pages).

* cited by examiner

OPTICAL COHERENCE TOMOGRAPHY WITH A FIZEAU-TYPE INTERFEROMETER

BACKGROUND

The following description is provided to assist the understanding of the reader. None of the information provided or references cited is admitted to be prior art.

Optical coherence tomography (OCT) is an imaging technique. OCT imaging techniques are often used in a medical setting. The techniques are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

OCT is often accomplished with the use of an interferometer. An interferometer utilizes light that is reflected back from a sample and a reference light. The reference light is generally configured to travel a similar distance as light that is reflected back from the sample. The light from the sample and the reference light can be combined in such a way that gives rise to an interference pattern. That is, the light from the sample and the reference light will either constructively or destructively interfere with each other. The level of interference that occurs indicates the reflectivity of areas of the sample, such that structures within the sample may be identified and imaged.

SUMMARY OF THE INVENTION

One embodiment relates to an optical system for generating an optical coherence tomography (OCT) image of a sample. The optical system includes a light source configured to generate and project an optical beam along an optical path. The optical system also includes a scanning element configured to receive the optical beam and direct the optical beam in a plurality of directions towards the sample. The optical system also includes a first lens disposed between the scanning element and the sample. The optical system also includes a reflective element disposed between the first lens and the sample, wherein the reflective element has a reflectivity within a range such that a first portion of the optical beam is transmitted through the reflective element to form a sample component beam and a second portion of the optical beam is reflected off of a surface of the reflective element to form a reference beam. The optical system also includes a detector configured to receive an interference signal generated by the sample beam and the reference beam.

Another embodiment relates to an OCT system. The OCT system includes a light source configured to generate an optical beam. The OCT system also includes a single-armed interferometer configured to receive the optical beam and produce an interference pattern. The single-armed interferometer includes scanning element configured to receive the optical beam and direct the optical beam in a plurality of directions towards a sample and a reflective element configured to divide the directed optical beam into a reference component beam and a sample component beam that reflects off of a sample. The OCT system also includes a detector configured to receive the interference pattern and produce an image signal. The OCT system also includes a processing circuit including a processor and a memory, the memory being structured to store instructions that are executable by the processor to cause the processor to receive the image signal from the detector and generate an OCT image based on the image signal.

Another embodiment relates to a method of using an OCT system. The method includes emitting an optical beam from a light source. The method also includes guiding, by an optical fiber, the optical beam along an optical path to a combined arm of a Fizeau-type interferometer. The method also includes directing, by a scanner, the optical beam in one of a plurality of different directions after emission of the optical beam from the optical fiber. The method also includes orienting, by a first lens, the optical beam towards a sample. The method also includes splitting, by a surface of a partial reflector, the optical beam into a reference component beam and a sample component beam, wherein the reference component beam reflects off the surface of the partial reflector and the sample component beam is transmitted through the partial reflector onto a sample. The method also includes directing, by the scanner, the reference component beam and a portion of the sample component beam reflected from the sample to a detector to generate an interference pattern.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
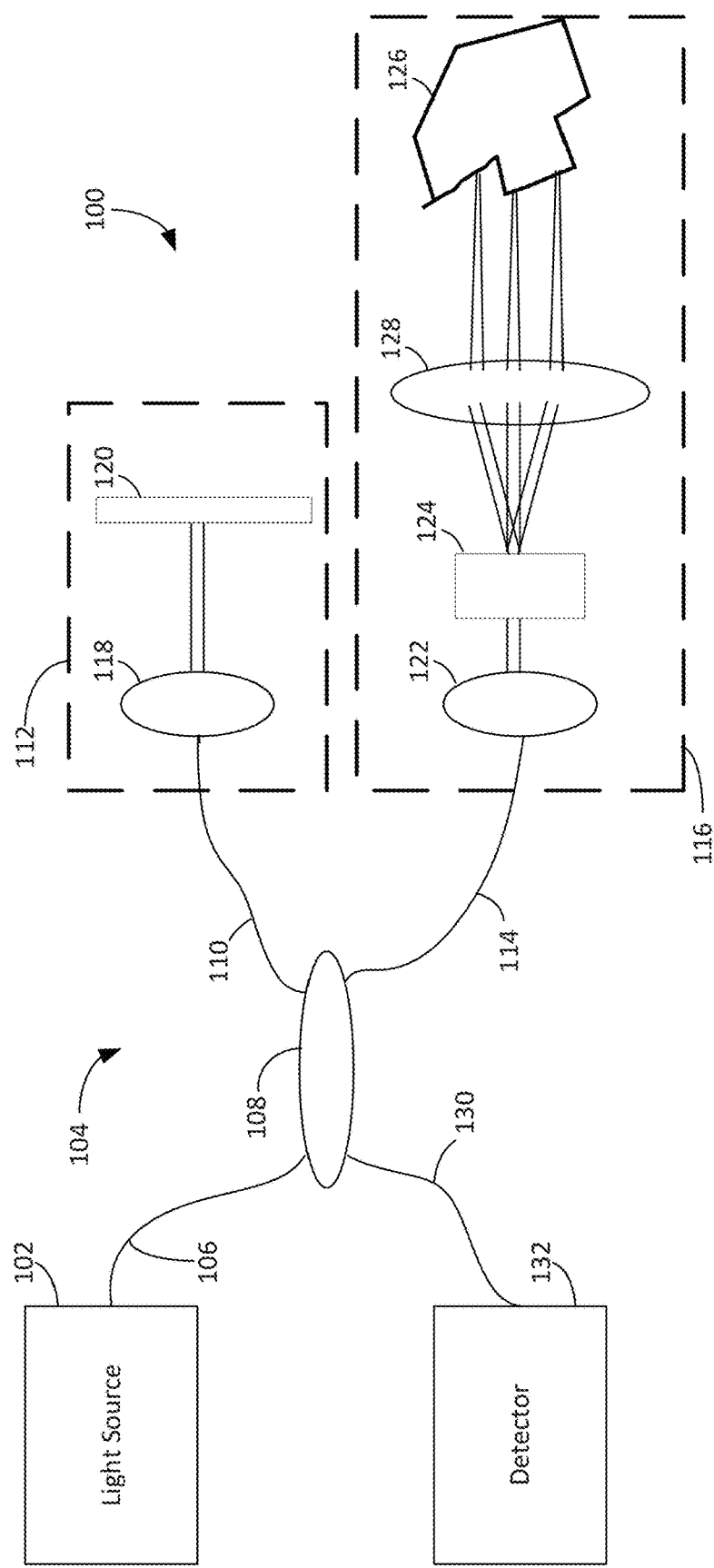
FIG. 1 depicts a representation of an optical coherence tomography (OCT) system in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an improved optical coherence tomography (OCT) system that includes a Fizeau-type interferometer. The OCT system beneficially combines the use of the Fizeau-type interferometer with telecentric beam scanning to enable multiple spatial positions on a sample to be imaged via a single-armed interferometer. As described herein, such a configuration allows for compact construction of OCT optical systems, reduces the need to correct for polarization variations induced by optical fibers, and reduces field distortion in a resulting three dimensional OCT images.

Generally, OCT systems utilize interferometers to divide a coherent optical beam emitted from a light source into a reference component beam and a sample component beam. Also, as it is desirable to make the OCT systems as compact as possible, OCT systems commonly employ optical fibers to control the optical path of the sample and reference component beams. To this end, OCT systems may employ an arrangement of optical components such as that depicted in FIG. 1. FIG. 1 depicts an OCT system 100 in accordance with an illustrative embodiment. The OCT system 100 includes a light source 102 and an optical fiber-based interferometer 104 (e.g., a Michelson-type interferometer). In the example shown, the optical fiber-based interferometer 104 includes a first optical fiber 106 that receives an optical beam emitted from the light source 102 and guides the optical beam to a fiber optic coupler 108. The fiber optic coupler 108 separates the optical beam into a reference component beam that is guided by a second optical fiber 110 into a reference arm 112 and a sample component that is guided by a third optical fiber 114 into a sample arm 116.

In the reference arm 112, the reference component beam is emitted from the second optical fiber into a first lens 118. In an embodiment, the first lens 118 collimates the reference component beam, which travels a reference path length to a reference mirror 120. In various embodiments, the reference path length is adjustable (e.g., via translation of the reference mirror 120) to perform time-domain OCT measurements. In some embodiments, the reference mirror 120 is held stationary to perform frequency-domain OCT measurements. The reference mirror 120 reflects the reference component beam back to the first lens 118, which re-focuses the reference component beam back into the second optical fiber 110 for transmittal back to the fiber optic coupler 108. In the sample arm 116, the sample component beam is emitted from the third optical fiber 114 into a second lens 122, which collimates the sample component beam. A scanner 124 directs the sample component beam along any one of a number of paths so as to cause the sample component beam to impinge upon a sample at a desired angle and/or location. A third lens 128 focuses the sample component beam onto the sample 126 at the desired location and/or angle. The sample component beam then reflects off the sample, is re-collimated via a second pass through the third lens 128, and redirected via the scanner 124 to the second lens 122, which refocuses the sample component beam into the third optical fiber 114 for transmission back to the fiber optic coupler 108.

Upon traveling from the sample arm 116 and the reference arm 112, respectively, the sample component beam and the reference component beam are combined at the fiber optic coupler 108 to generate a combined beam that includes an interference pattern. In various embodiments, the phase of the sample component beam differs from the phase of the reference component beam due the optical path difference of the component beams (e.g., the combined length of the second optical fiber 110 and the reference arm 112 may differ from the combined length of the third optical fiber 114 and the sample arm 116). Based on the phase difference, the reference component beam and the sample component beam may constructively or destructively interfere with one another to produce the interference pattern. The combined beam is then split at the fiber optic coupler 108. Half of the combined beam is then transmitted down the first optical fiber 106 and towards the light source 102. The other half is transmitted down a fourth optical fiber 130 to a detector 132, which receives the interference pattern and may use the interference pattern in combination with a number of other interference patterns (e.g., produced by different configurations of the scanner 124) to generate an OCT image of the sample 126.

The configuration of the OCT system 100 has some drawbacks. For example, due to the utilization of the fiber optic coupler 108, half of the combined beam is directed back towards the light source 102 via the first optical fiber 106. Such a splitting of the combined beam results in a loss of signal power provided to the detector 132, which may result in a lower resolution OCT image. Furthermore, the combined beam may damage the light source 102.

Other drawbacks of the OCT system 100 relate to the inclusion of both the reference arm 112 and the sample arm 116. For example, the inclusion of both the reference arm 112 and the sample arm 116 necessitates the inclusion of both the second and third optical fibers 110 and 114. Optical fibers oftentimes induce polarization variations in optical beams contained therein. Such polarization variations may depend on various factors, such as temperature, bends or kinks in the fiber, and mechanical stresses placed on the fiber. Because these factors may vary from fiber to fiber, the state of polarization of the reference component beam and the sample component beam may differ from one another resulting in alterations to the interference pattern when the beams are combined at the fiber optic coupler 108. This results in a fading of the signal received at the detector 132, and thus a diminished image quality. As such, the OCT system 100 benefits from the incorporation of polarization controlling components (e.g., rotators) within the reference and sample arms 112 and 116. Such incorporations, however, add to the complexity and size of the OCT system 100.

Additionally, the separation of the reference component beam from the scanner 124 results in increased distortion in the OCT image that is eventually generated. In the OCT system 100, for example, when the scanner 124 is configured such that the sample component beam impinges on the third lens 128 at a relatively low incident angle, the optical path length travelled by the sample component beam will be smaller in the most of lenses than when the scanner 124 is configured such that the sample component beam impinges on the third lens 128 at a relatively high angle. This is at least in part because the curvature of the third lens 128 may introduce field curvature (e.g., Petzval field curvature) into the sample component beam that is not introduced into the reference component beam. Such differences between the sample component beam and the reference component beam result in distortions in the OCT image. Additionally, the scanner 124 may induce distortions on the sample component beam, further reducing OCT image quality.

Figure 2:
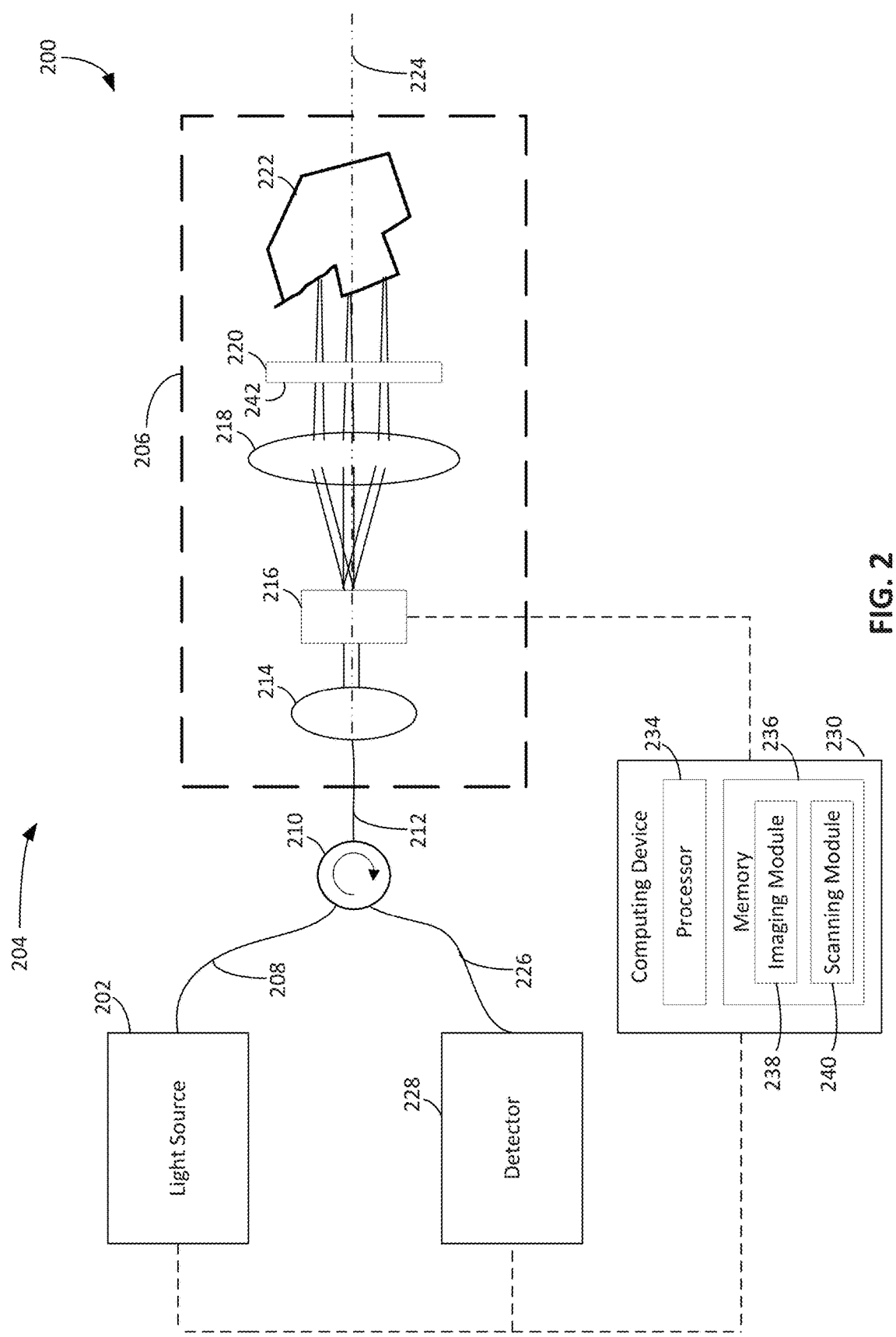
FIG. 2 depicts a representation of an OCT system including a Fizeau-Type interferometer in accordance with an illustrative embodiment.

FIG. 2 depicts an OCT system 200 in accordance with an illustrative embodiment. In the example shown, the OCT system 200 includes a light source 202 and a Fizeau-type interferometer 204. The Fizeau-type interferometer 204 is specifically designed to alleviate the above-described deficiencies of the OCT system 100 described with respect to FIG. 1.

The Fizeau-type interferometer 204 includes a combined arm 206 configured to produce both a sample component beam and a reference component beam. As such, in the OCT system 200, the sample component beam and the reference component beam travel along the same set of optical fibers. Given this, whatever polarization variations induced in the reference and sample component beams by the optical fibers will be substantially identical to one another, reducing diminutions in interference pattern quality. Additionally, by combining the sample arm and the reference arm into the combined arm 206, the configuration of the OCT system 200 requires fewer components than the OCT system 100.

In the example shown, the Fizeau-type interferometer 204 includes a first optical fiber 208 configured to guide an optical beam emitted by the light source 202 to an optical element 210. The optical element 210 is configured to receive the optical beam and guide the optical beam to the combined arm 206 by way of a second optical fiber 212. In some embodiments, the optical element 210 is also configured to receive combined signal and reference component beams from the combined arm 206 and guide the combined beams to a detector 228 via a third optical fiber 226. In the example shown, the optical element 210 is a fiber optical circulator including a first port, a second port, and a third port. In the example shown, the fiber optical circulator is configured to direct an optical beam received from the first port (e.g., from the first optical fiber 208) through the second port (e.g., along a second optical fiber 212 towards the combined arm 206) and direct an optical beam received from the second port (e.g., from the second optical fiber 212) through the third port (e.g., along a third optical fiber 226 to the detector). As such, the optical beam from the light source 202 is never split, which increases the intensity of the interference signal received by the detector 228 and enhances image quality. However, in various alternative embodiments, the optical element 210 may include a fiber optical coupler or a beam splitter without departing from the scope of the present disclosure.

Once directed to the second optical fiber 212 via the optical element 210, the optical beam is emitted at the combined arm 206. The combined arm 206 includes a first lens 214, a scanner 216, a second lens 218, a reflective element 220, and a sample 222. In an embodiment, each of the first lens 214, the scanner 216, the second lens 218, and the reflective element 220 define a common optical axis 224 of the combined arm 206, although the independent optical axes of any one of the first lens 214, the scanner 216, the second lens 218, and the reflective element 220 may be offset from one another without departing from the scope of the present disclosure.

In the example embodiment shown, the combined arm 206 does not include any optical fibers. In other words, once the optical beam is emitted from the second optical fiber 212, the optical beam generally travels through the ambient (or controlled) environment of the OCT system 200. Such a configuration facilitates wide field of view scanning of the sample 222 because, if a fiber were placed in the combined arm 208, a limited angle of incidence would need to be maintained so as to maintain total internal reflection of the optical beam in the fiber. Additionally, since the optical beam is separated into sample and reference components within the combined arm 206, the inclusion of fibers in the combined arm 206 would result in the sample and reference components propagating through separate optical fibers (or separate portions of the same optical fiber), which would result in polarization variations between the sample and reference component beams. Thus, the fiber-free combined arm facilitates angular scanning of the sample 222 and improves image quality.

The first lens 214 is configured to receive the optical beam once the optical beam is emitted from the second optical fiber 212. In an embodiment, the second optical fiber 212 is arranged such that, upon emission therefrom, the optical beam is centered along the optical axis 224. In an embodiment, the first lens is a fiber collimator including a positive (e.g., bi-convex) lens physically connected to the second optical fiber 212 and configured to collimate the optical beam at the optical axis 224 such that the optical beam travels substantially along the optical axis 224. After collimation, the optical beam impinges on the scanner 216.

In some embodiments, the scanner 216 is galvanometric scanner including at least one mirror. In an embodiment, the galvanometric scanner includes a rotary motor configured to rotate based on control signals received from a computing device 230, thereby varying the propagation direction of the optical beam. As such, after being reflected by the mirrors of the scanner 216, the optical beam may propagate at an angle to the optical axis 224. It should be understood that the scanner 216 may be a refractive device (e.g., a pair of wedge prisms) or any other type of scanner without departing from the scope of the present disclosure.

After being redirected by the scanner 216, the optical beam impinges on the second lens 218 at a position that is dependent on the orientation of the scanner 216. For example, in an embodiment where the scanner 216 is configured to redirect the optical beam horizontally away from the optical axis 224, the optical beam may impinge on a first surface of the second lens 218 at a position that is horizontally offset from the optical axis 224 by a distance that is dependent on the orientation of the scanner 216. As will be appreciated, the propagation direction of the optical beam after refracting through the second lens 218 is dependent on the optical characteristics of the second lens 218 (e.g., the radii of curvature of the surfaces of the second lens, which define the positioning of the focal planes of the second lens).

In an embodiment, the distance along the optical axis 224 between the center of the scanner 216 and a principal plane of the second lens 218 corresponds to a rear focal distance of the second lens 218. As such, irrespective of the direction at which the optical beam initially impinges on the second lens 218, the optical beam emerges in a direction that is substantially parallel to the optical axis 224. In other words, such a configuration enables telecentric scanning of various positions of the sample 222 through varying the orientation of the scanner 216.

The reflective element 220 is disposed between the second lens 218 and the sample 222. The reflective element 220 is an optical element having a reduced reflectivity within the spectral range of the light source 202. For example, in one embodiment, the reflective element 220 is a partial reflector having a reflectivity of less than 50% in the near infrared spectrum. However, in various embodiments, the reflective element 220 has a non-zero reflectivity such that a portion of the optical beam reflects off of a surface 242 of the reflective element 220 to generate a reference beam for the Fizeau-Type interferometer 204. In the example shown, the surface 242 is the surface of the reflective element 220 that is nearest to the second lens 218. In alternative embodiments, the optical beam may be transmitted through at least a portion of the reflective element 220 prior to being partially reflected to generate the reference component beam.

Also in the example shown, the surface 242 is substantially planar such that, upon reflection off the surface 242, the reference component beam travels in a direction that is parallel to the optical beam's incidental direction (e.g., parallel to the optical axis 224). Such a configuration simplifies the structure of the Fizeau-Type interferometer 204, as the reference component beam is directed via the second lens 218 and the scanner 216 back to the second optical fiber 212. Additionally, as discussed with respect to FIGS. 3-4, providing a planar surface 242 ensures that distortions in the OCT image resulting from variations in the orientation of the scanner 216 are minimized.

Additionally, because the reflectivity of the reflective element 220 is non-unitary, a portion of the optical beam is transmitted (e.g., refracts) through the reflective element 220 to form a sample component beam of the Fizeau-type interferometer 204. The sample component beam then reflects off of a portion (e.g., a surface or an inner portion) of the sample 222 and is redirected back through the reflective element 220, second lens 218, scanner 216, and first lens 214 into the second optical fiber 212, and thereby guided to the optical element 210, which directs the reflected reference component and sample component beams (hereafter referred to as "the combined beam") to a detector. Phase differences in the sample component beam and the reference component beam resulting from differences between optical path lengths of the sample and reference component beams cause the combined beam to contain an interference pattern. Such differences in optical path length are dependent on properties of the sample 222 (e.g., the topography of surfaces of various features within the sample 222). As such, the interference pattern includes information pertaining to various features of the sample 222, and may be used to generate an image of the sample 222.

In some embodiments, a desired surface of the sample 222 (e.g., an exterior surface of the sample 222) is placed at a distance from a principal plane (e.g., a secondary principal plane) of the second lens 218 such that the sample component beam has a desired spot size upon reaching the sample 222. For example, in one embodiment, the desired surface of the sample is placed at a second focal point of the second lens 218 such that the spot size of the sample component beam is minimized upon reaching the desired surface of the sample 222. In other embodiments, the desired surface of the sample 222 is offset from the second focal point of the second lens 218 such that the sample component beam reaches a minimum spot size within the sample 222.

In one embodiment, the second lens 218 includes a bi-convex lens having a single focal point. In such embodiments, the scanner 216 may be placed at a focal plane of the second lens 218 such that the optical beam is collimated upon refracting through the second lens. As such, the sample component beam may maintain a constant spot size after being transmitted through the reflective element 220. It should be understood that the combined arm 206 may include any number of additional optical components without departing from the scope of the present disclosure. For example, in some embodiments, the combined arm 206 includes a system of lenses configured to expand or contract the sample beam prior to when the sample beam impinges upon the sample 222.

The third optical fiber 226 is configured to guide the combined beam including the interference pattern to the detector 228, which is configured to generate an image signal based on the combined beam. As will be understood, the structure of the detector 228 may vary depending on the implementation of the OCT system 200. For example, in embodiments where the OCT system 200 is configured to generate OCT images of the sample via Fourier-domain OCT, the detector 228 includes a charge-coupled device (CCD) array including a plurality of pixels configured to generate an electrical current based on the photons of the combined optical beam. In some embodiments, a diffractive element (e.g., grating) is positioned in front of the detector 228 such that the spatial position with which the interference signal impinges on the detector 228 is dependent on the spectrum of the interference signals. As such, the detector 228 may produce a plurality of time-varying electrical signals corresponding to spectral subcomponents of the interference pattern. Based on the magnitude of these electrical signals, the OCT system (e.g., via the computing device 230) may identify the depth of various surfaces within the sample 222. In some embodiments, where, for example the light source 202 is a swept laser, the detector 228 may include a photodiode detector.

The computing device 230 is configured to operate various components of the OCT system 200 to generate OCT images of the sample 222 based on the interference patterns generated via the Fizeau-type interferometer 204. In this regard, the computing device 230 is communicably coupled to at least the light source 202, scanner 216, and detector 228. It should be understood that the computing device 230 may be communicably coupled to any component of the OCT system 200 without departing from the scope of the present disclosure. Additionally, it should be understood that the light source 202, scanner 216, and any other optical component of the OCT system 200 may include an independent controller without departing from the scope of the present disclosure.

The computing device 230 includes a processor 234 and a memory 236. Processor 234 may be a general purpose or specific purpose processor, an application specific integrated circuit (ASIC), one or more field programmable gate arrays (FPGAs), a group of processing components, or other suitable processing components. Processor 234 may be configured to execute computer code or instructions stored in memory 236 or received from other computer readable media (e.g., CDROM, network storage, a remote server, etc.) to perform one or more of the processes described herein. Memory 236 may include one or more data storage devices (e.g., memory units, memory devices, computer-readable storage media, etc.) configured to store data, computer code, executable instructions, or other forms of computer-readable information. Memory 236 may include random access memory (RAM), read-only memory (ROM), hard drive storage, temporary storage, non-volatile memory, flash memory, optical memory, or any other suitable memory for storing software objects and/or computer instructions. In some embodiments, the computing device 230 also includes a user interface (not shown). The user interface may include a display or other element (e.g., a button, joystick, etc.) capable of receiving an operator input to adjust any of the operational parameters of any of the components of the OCT system 200.

As shown in FIG. 2, the memory 236 includes an imaging module 238 and a scanning module 240. It should be understood that the memory 236 may include more, less, or different modules without departing from the scope of the present disclosure. The scanning module 240 is structured to cause the processor 234 to provide control signals to various components of the OCT system 200 to generate a set of image signals with which to generate an OCT image. In this regard, via the scanning module 240, the computing device 230 may provide control signals to the light source 202 and the scanner 216 to cause the light source 202 to emit an optical beam having a desired set of characteristics (e.g., beam size, spectral range) and the scanner 216 to direct the optical beam at a desired position on the sample 222.

In various embodiments, the control signals provided via the scanning module 240 are dependent on a mode of operation of the OCT system 200. For example, in some embodiments, the light source 202 is a swept light source configured to produce a narrow bandwidth output that cycles through a spectral range within a predetermined period. In some embodiments, the narrow bandwidth output may have a coherence length of 10 mm or larger.

The control signals provided by the computing device 230 may cause the scanner 216 to remain at a particular angle for a predetermined number of such time periods to enable a plurality of scans (e.g., A scans via scanning the swept light source 202 through multiple cycles) to be performed. After the light source 202 is scanned a predetermined number of times, the scanner 216 may be adjusted by a predetermined angular amount, and the cycles of the light source 202 may be repeated. As such, various portions of the sample 222 are imaged throughout the entire spectral range of the swept light source 202, enabling the depth of various surfaces or other features in the sample 222 to be determined at various spatial positions in the sample 222. The scanner 216 may be controlled differently (e.g., left at a certain angular position for a longer or shorter period) in embodiments where the OCT system 200 is configured to generate an OCT image using Fourier-domain OCT.

The imaging module 238 is configured to generate an OCT image of the sample 222 using the image data produced by the detector 228. For example, for each respective position of the scanner 216, the imaging module 238 may cause the processor 234 to sample the image signal produced by the detector 228 and produce a scan line with the sampled signal via the Fast Fourier Transform algorithm. After such a process is repeated for various positions of the scanner 216, the imaging module 238 may combine the scan lines to produce a two dimensional or three dimensional OCT image of the sample 222. As will be appreciated, the imaging module 238 may cause the processor 234 to perform a number of additional operations (e.g., application of an image enhancement filter, dispersion compensation) on the image data to further enhance the quality of the OCT image. Any image processing techniques may be used in accordance with the present disclosure.

Figure 3:
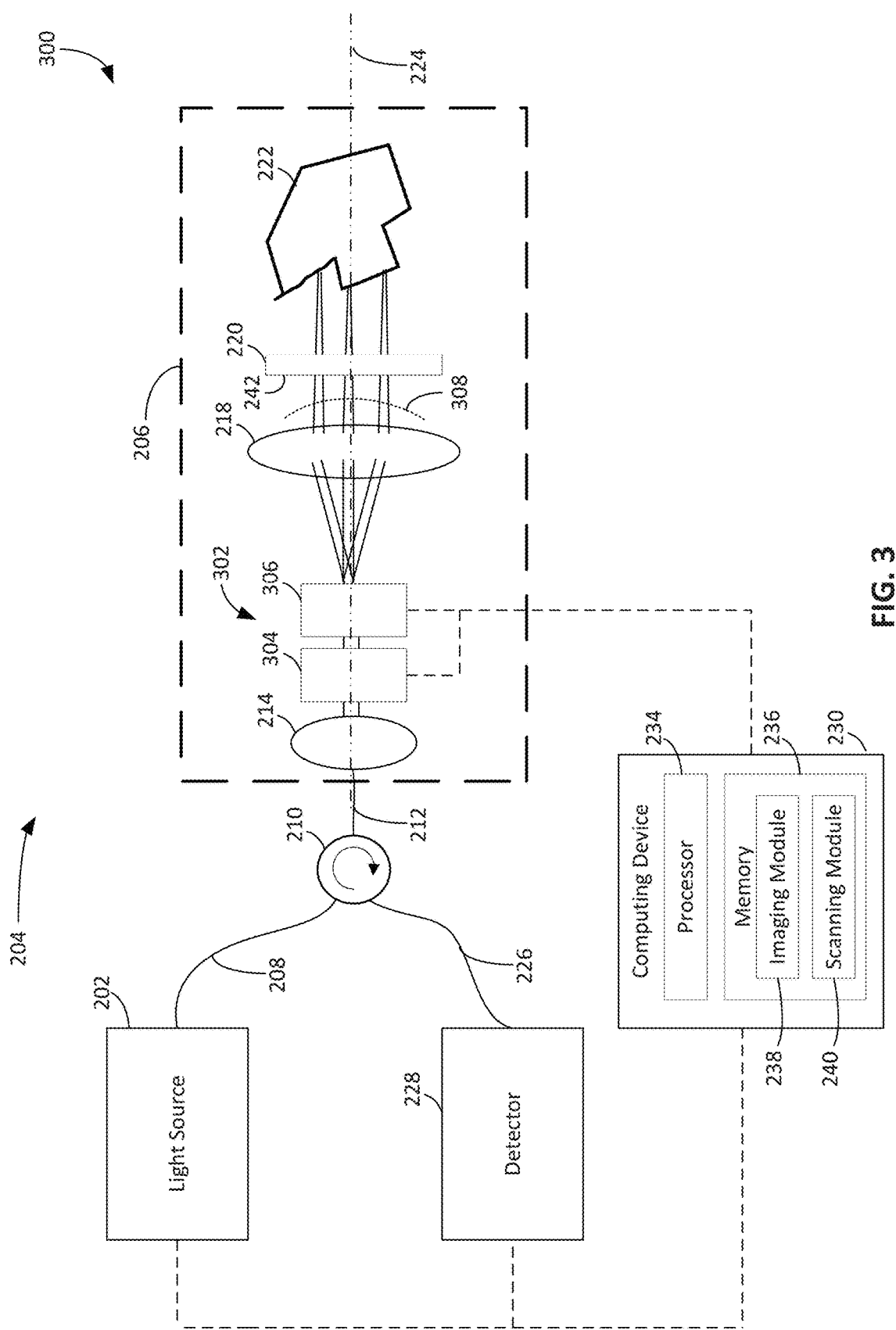
FIG. 3 depicts a representation of an OCT system including a Fizeau-Type interferometer with a multi-directional scanner in accordance with an illustrative embodiment.

Referring now to FIG. 3, an OCT system 300 is shown in accordance with an illustrative embodiment. OCT system 300 shares many of the same features as the OCT system 200. Accordingly, similar reference numerals are used in FIG. 3 to describe such similar features.

The OCT system 300 differs from the OCT system 200 in that the OCT system 300 includes scanner 302 that differs from the scanner 216 discussed with respect to FIG. 2. The scanner 302 includes a first scanning element 304 and a second scanning element 306. In one embodiment, the first scanning element 304 is configured to scan the optical beam in a first (e.g., horizontal) direction and the second scanning element 306 is configured to scan the optical beam in a second (e.g., vertical direction). In various embodiments, the first and second scanning elements 304 and 306 include galvanometric scanning mirrors that are rotatable about respective axes of rotation at various angels to cause the angular direction of the optical beam to vary. In other alternative embodiments, the first and second scanning elements 304 and 306 include refractive optical elements (e.g., wedge prism pairs at ends of variable gaps).

The scanner 302 thus enables three dimensional OCT images of the sample to be captured. For example, in one embodiment, the computing device 230 (e.g., via the scanning module 240) may control the scanner 302 to obtain a series of scan lines of the sample along a first line in the sample (e.g., by scanning the light source 202 at a number of times while the first scanning element 304 is in at various different angles, holding the second scanning element 306 constant), adjust the position of the second scanning element 306 to obtain another series of scan lines at a second vertical position, and repeat this process until data has been gathered for a desired portion of the sample 222. After gathering this data, the computing device 230 (e.g., via the imaging module 238) may combine the scan lines to obtain a three dimensional OCT image of the sample 222.

In a preferred embodiment, the surface 242 of the reflective element 220 that reflects a portion of the optical beam to generate the reference component beam is planar and extends in a direction that is perpendicular or substantially perpendicular to the optical axis 224. In such an embodiment, since the optical beam is collimated by the second lens 218 (or since the optical beam travels parallel or substantially parallel to the optical axis 224), the optical path length between the sample 222 and the surface 242 is the same irrespective of the optical beam's direction of propagation prior to reaching the second lens 218.

Such a configuration ensures that fan or field distortion in the eventual OCT image is minimized. Since there are multiple scanning elements (e.g., the first scanning element 304 and the second scanning element 306) in the scanner 302, the optical path length of the optical beam varies depending on the relative positioning of such scanning elements. For example, the optical path length will be minimized when the first scanning element 304 is oriented parallel to the second scanning element 306, but will increase as the orientation of the scanning elements 304 and 306 are changed to differ from one another. Such increases in optical path length cause the optical beam to form an elliptical wave front 308 between the scanner 302 and the sample 222. Two potentially negative side effects emerge from such a tendency. First, due to the differing optical path, one cannot position the scanner 302 exactly at a focal plane of the second lens 218, which means that the optical beam will not be parallel to the optical axis 224 upon emerging from the second lens 218, which induces distortion in the optical beam. Second, this difference in optical path length causes differences between the optical path length of the reference component beam and the sample component beam that are unrelated to the characteristics of the sample 222.

Figure 4:
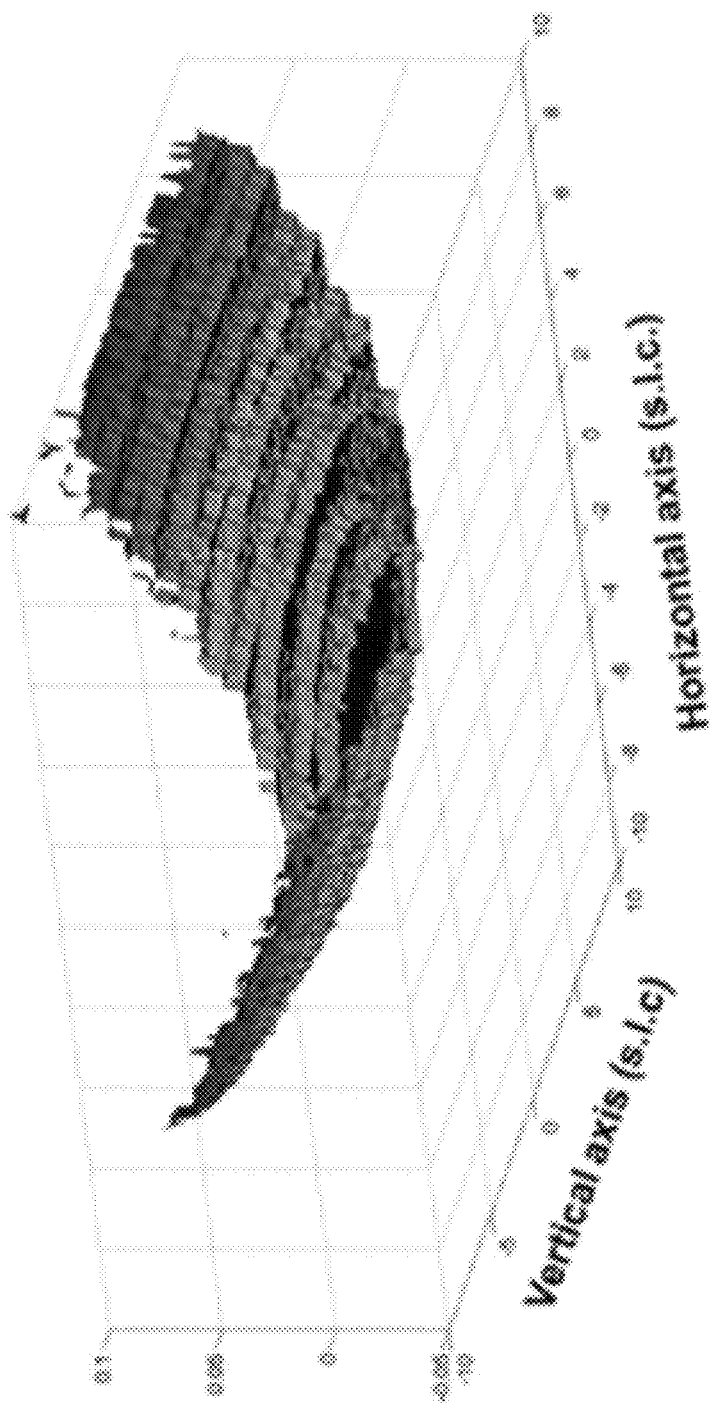
FIG. 4 depicts measurements of fan distortion in relation to various scanning directions of an OCT system in accordance with an illustrative embodiment.

These optical path length differences can produce a significant amount of fan distortion in an OCT image. For example, FIG. 4 shows a plot of the amount of fan distortion produced depending on the vertical and horizontal positioning of a scanner. As shown, the amount of fan distortion is basically proportional to the magnitude of the horizontal position of the scanner. The measurements shown in FIG. 4 were taken using an OCT system including a Michelson interferometer (e.g., an interferometer similar to the interferometer 104 discussed with respect to FIG. 1) where the reference beam and the sample beam are split prior to reaching the scanner. As a result, the optical path length differences induced on the sample beam via the scanner are not imparted on the reference beam. This creates optical path differences in the sample and reference component beams that are unrelated to the sample 222 and thus distorts resulting OCT images. To correct for such distortion, complex computational algorithms must be used.

The configuration of the OCT system 300, however, largely eliminates such fan distortion. Specifically, since the sample component beam and the reference component beam are not separated prior to reaching the scanner 302, any optical path length differences resulting from the relative positioning of the first and second scanning elements 304 and 306 are applied equally to the reference component beam and the sample component beam. As such, the sample and reference component beams emerge from the scanner 302 having a constant phase relationship which minimizes distortion.

The planarity of the surface 242 of the reflective element 220 also facilitates the minimization of fan distortion. Since the surface 242 is planar, the optical path length for the sample component beam remains relatively constant irrespective of the positioning of the sample component beam. Such a configuration eliminates the introduction of additional phase differences between the sample and reference component beams, and further reduces the amount of algorithmic correction that needs to be done to the image. Additionally, any distortions resulting from a mismatch between the positioning of the scanner 302 and a focal plane of the second lens 218 will also be imparted on both the sample component beam and the reference component beam. Thus, the distortions will tend to cancel one another in the interference pattern.

Figure 5:
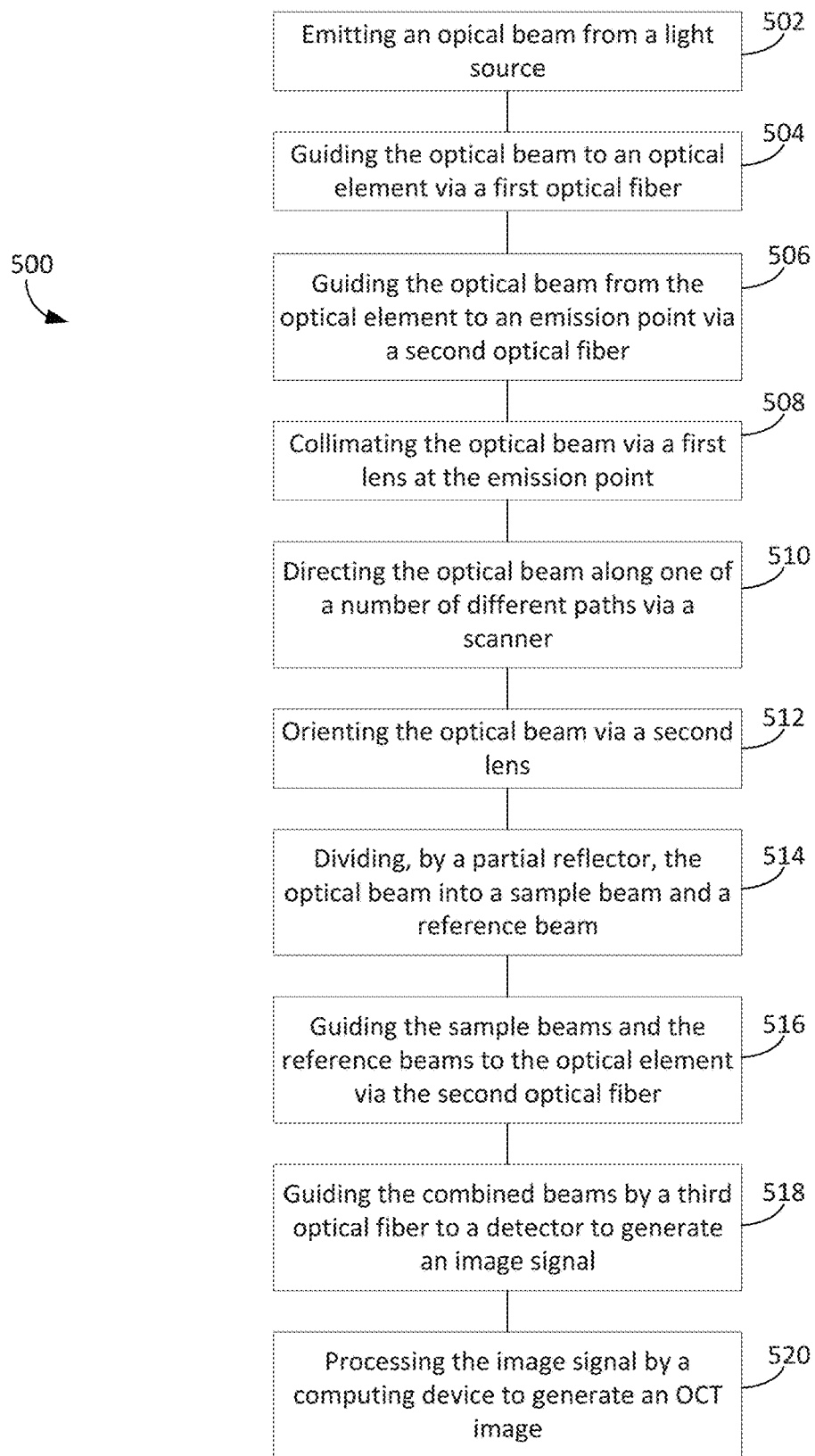
FIG. 5 depicts a method of using an OCT system in accordance with an illustrative embodiment.

FIG. 5 illustrates a method 500 of operation of an OCT system in accordance with an illustrative embodiment. In an operation 502, an optical beam is emitted from a light source. In one embodiment, the light source is a swept laser source configured to scan a number of spectral ranges in the near infrared spectrum. In another embodiment, the light source is a broadband pulsed laser. In an operation 504, the optical beam is guided to an optical element via a first optical fiber. In an embodiment, the first optical fiber (or any other optical fibers referred to herein) may be single mode optical fibers. The optical element may be a fiber optic coupler or a circulator configured to guide the optical beam to a second optical fiber (which, in some embodiments, is an extension of the first optical fiber).

In an operation 506, the optical beam is guided along the second optical fiber to an emission point. In an operation 508, the optical beam is collimated upon emission from the second optical fiber via a first lens. In some embodiments, the first lens is a fiber optic collimator attached or coupled to the second optical fiber. The first lens may be a positive (e.g., bi-convex) lens. Upon collimation, the optical beam is directed along one of a number of different paths via a scanner in an operation 510. As described herein, the scanner may include a single scanning element (e.g., to generate two dimensional OCT images of a sample) or multiple scanning elements (e.g., to generate three dimensional OCT images of the sample). Each of the scanning elements may include reflective, refractive, or any other type of scanning element. The scanner is configured to direct the optical beam in a desired direction. In some embodiments, the desired direction is determined by a computing system based on a previous orientation of the scanner.

In an operation 512, the optical beam is oriented via a second lens. In one embodiment, the distance between a center of the scanner and a principal plane of the second lens corresponds to a focal length of the second lens such that the optical beam, upon emerging from the second lens, travels in a direction that is substantially parallel to an optical axis of the second lens. In various embodiments, the second lens may include a positive (e.g., bi-convex) lens. In an operation 514, after being oriented by the second lens, the optical beam is divided into a sample component beam and a reference component beam via a partial reflector. In an embodiment, the partial reflector includes a surface disposed nearest to the second lens that is substantially planar and has a limited (e.g., 10%) reflectivity in the near infrared. Preferably, the surface is substantially planar and oriented substantially perpendicular to the optical axis of the second lens. As such, the portion of the optical beam that is reflected from the surface travels in a direction that is parallel to the optical axis of the second lens to form the reference component beam. The portion of the optical beam that is transmitted through the partial reflector then impinges upon a sample, and at least a portion thereof reflects in a direction that is substantially parallel to the optical axis of the second lens.

As such, upon being reflected from the sample, a portion of the sample beam travels back through the second lens, scanner, and first lens along with the reference component beam. In an operation 516, the sample and reference component beams are guided back to the optical element via the second optical fiber, where the component beams are combined to form a combined beam. Due to path length differences between the sample component beam and the reference component beam, the component beams will have a different phase. Assuming that the phase difference is within the coherence length of the light source 202, the combining of the reference and sample component beams produces an interference pattern. In an operation 518, the combined beam is guided via a third optical fiber to a detector to generate an image signal. In an embodiment, the detector includes a photodiode producing a time-varying electrical current that is dependent on the interference pattern. In an operation 520, the image signal is provided to a computing device for processing. The image signal may be combined with various other image signals to produce an OCT image of the sample.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Additional embodiments may be set forth in the following claims.

What is claimed is:

1. An optical system for generating an optical coherence tomography (OCT) image of a sample, the optical system comprising:
   a light source configured to generate and project an optical beam along an optical path;
   a scanning element configured to receive the optical beam and direct the optical beam in a plurality of directions towards the sample;
   a first lens disposed between the scanning element and the sample, wherein the scanning element is disposed in a rear focal plane of the first lens to enable telecentric scanning of the sample by varying an orientation of the scanning element;
   a reflective element disposed between the first lens and the sample, wherein the reflective element has a reflectivity within a range such that a first portion of the optical beam is transmitted through the reflective element to form a sample component beam and a second portion of the optical beam is reflected off of a surface of the reflective element to form a reference beam; and
   a detector configured to receive an interference signal generated by the sample beam and the reference beam.

2. The optical system of claim 1, further comprising a second lens disposed between the light source and the scanning element, wherein the second lens is configured to collimate the optical beam prior to the optical beam reaching the scanning element.

3. The optical system of claim 1, further comprising an optical element configured to guide the interference signal to the detector.

4. The optical system of claim 3, wherein the optical element is also configured to receive the optical beam upon emission of the optical beam from the light source to direct the optical beam down the optical path.

5. The optical system of claim 4, further comprising a first optical fiber configured to guide the optical beam to the optical element and a second optical fiber configured to guide the optical beam to the second lens from the optical element.

6. The optical system of claim 5, wherein the optical element comprises a fiber circulator including a first port configured to receive the optical beam emitted by the light source, a second port configured to direct light received from the first port down the second optical fiber, and a third port configured to direct the reference beam and the sample beams down a third optical fiber to the detector.

7. The optical system of claim 1, wherein the surface of the reflective element is planar.

8. The optical system of claim 1, wherein the light source is a swept laser source having a coherence length of 10 mm or larger.

9. An OCT system comprising:
   a light source configured to generate an optical beam;
   a single-armed interferometer configured to receive the optical beam and produce an interference pattern, the single-armed interferometer comprising:
      a scanning element configured to receive the optical beam and direct the optical beam in a plurality of directions towards a sample;
      a first lens, wherein the scanning element is disposed in a rear focal plane of the first lens to enable telecentric scanning of the sample by varying an orientation of the scanning element; and
      a reflective element configured to divide the directed optical beam into a reference component beam and a sample component beam that reflects off of a sample;
   a detector configured to receive the interference pattern and produce an image signal; and
   a processing circuit including a processor and a memory, the memory being structured to store instructions that are executable by the processor to cause the processor to receive the image signal from the detector and generate an OCT image based on the image signal.

10. The OCT system of claim 9, wherein the single-armed interferometer includes optical fibers and a second lens, wherein the optical fibers are configured to direct the optical beam to the second lens, wherein the second lens is configured to collimate the optical beam as it emerges from the optical fibers.

11. The OCT system of claim 10, wherein the scanning element is disposed between the first lens and the second lens, and wherein the first lens is configured to direct the sample component beam onto the surface of the sample.

12. The OCT system of claim 9, wherein a surface of the reflective element is planar.

13. The OCT system of claim 9, wherein the OCT image is generated using the Fourier domain method.

14. The OCT system of claim 9, wherein the light source is a swept laser source having a coherence length of 10 mm or larger.

15. A method of using an OCT system comprising:
   emitting an optical beam from a light source;
   guiding, by an optical fiber, the optical beam along an optical path to a combined arm of a Fizeau-type interferometer;

directing, by a scanner, the optical beam in one of a plurality of different directions after emission of the optical beam from the optical fiber;

orienting, by a first lens, the optical beam towards a sample, wherein the scanner is disposed in a rear focal plane of the first lens, and wherein the orienting the optical beam comprises varying an orientation of the scanner to telecentrically scan the sample;

splitting, by a surface of a partial reflector, the optical beam into a reference component beam and a sample component beam, wherein the reference component beam reflects off the surface of the partial reflector and the sample component beam is transmitted through the partial reflector onto a sample; and directing, by the scanner, the reference component beam and a portion of the sample component beam reflected from the sample to a detector to generate an interference pattern.

16. The method of claim 15, further comprising collimating, by a second lens, the optical beam upon emission of the optical beam from the optical fiber prior to the directing of the optical beam by the scanner.

17. The method of claim 15, wherein the surface of the partial reflector is planar and oriented perpendicular to an optical axis of the second lens.

* * * * *